United States Patent [19]

Dworkin

[11] 4,187,239
[45] Feb. 5, 1980

[54] METHOD FOR PREPARING ORGANOTIN COMPOUNDS

[75] Inventor: Robert D. Dworkin, Old Bridge, N.J.

[73] Assignee: M&T Chemicals Inc., Woodbridge, N.J.

[21] Appl. No.: 926,516

[22] Filed: Jul. 20, 1978

Related U.S. Application Data

[63] Continuation-in-part of Ser. No. 738,132, Nov. 2, 1976.

[51] Int. Cl.² ............................................. C07F 7/22
[52] U.S. Cl. .................... 260/410.6; 260/399; 260/410; 260/429.7
[58] Field of Search .............. 260/429.7, 410.6, 410, 260/399

[56] References Cited

U.S. PATENT DOCUMENTS

| | | | |
|---|---|---|---|
| 2,832,750 | 4/1958 | Weinberg et al. | 260/45.75 S |
| 2,870,182 | 1/1959 | Leistner et al. | 260/429.7 |
| 2,885,415 | 5/1959 | Ramsden | 260/429.7 |
| 3,565,931 | 2/1971 | Brecker | 260/429.7 |
| 3,931,263 | 1/1976 | Mott | 260/429.7 |
| 3,979,359 | 9/1976 | Kugele et al. | 260/45.75 S |
| 4,124,618 | 11/1978 | Dworkin et al. | 260/429.7 X |
| 4,124,618 | 11/1978 | Dworkin et al. | 260/410.6 |

Primary Examiner—Helen M. S. Sneed
Attorney, Agent, or Firm—Kenneth G. Wheeless; Robert Spector

[57] ABSTRACT

Organotin derivatives of mercaptoalcohol esters that correspond to the general formula

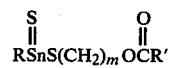

or

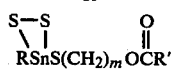

wherein R and R' are hydrocarbon and m is 2 or 3, are prepared by sequentially reacting a monoorganotin trihalide with stoichiometric amounts of a base, a mercaptoalcohol, an alkali metal sulfide or disulfide and a carboxylic acid or an ester thereof. The present method offers advantages over the prior art, which teaches reacting an esterified mercaptoalcohol with an organotin halide, oxide or organostannoic acid. Compounds wherein R' is n-heptyl are unique in that they do not exhibit the disagreeable odor that characterizes this class of compounds.

11 Claims, No Drawings

METHOD FOR PREPARING ORGANOTIN COMPOUNDS

BACKGROUND

This application is a continuation-in-part of application Ser. No. 738,132, filed Nov. 2, 1976 now U.S. Pat. No. 4,124,618.

This invention relates to a method for preparing a particular class of organotin compounds. This invention further relates to a method for preparing organotin derivatives or mercaptoalcohol esters which offers advantages with respect to known methods for preparing this class of organotin compounds.

U.S. Pat. No. 2,870,182 discloses compounds of the general formula $R_nSnA_{4-n}$ wherein R represents one of a specified group of hydrocarbon radicals, n is 1, 2 or 3 and A represents the residue obtained following removal of the hydrogen atom from the —SH group of a mercaptoalcohol ester. The patent further discloses that compounds corresponding to the foregoing formula can be prepared by first reacting the mercaptoalcohol with a carboxylic acid in the presence of a suitable esterification catalyst and subsequently reacting the resultant ester with an organotin halide, oxide or an organostannoic acid. This preparative method is less than desirable for a number of reasons. Firstly, formation of the mercaptoalcohol ester is an equilibrium reaction which almost always requires an acidic catalyst and removal of water during the reaction to obtain a useful yield of the desired product within a reasonable length of time. The acid catalyst may promote a number of undesirable side reactions, including polymerization of the mercaptoalcohol. The polymer may contain end groups that will subsequently react with the organotin compound, however the reaction product is not nearly as effective as the desired monomeric ester derivative in a number of applications, including stabilization of vinyl chloride polymers. A second undesirable feature of the aforementioned prior art method is that removal of water is required during preparation of the ester and during reaction of the ester with the organotin compound. Removal of water requires heating, which not only increases processing costs due to the additional energy input but can result in larger amounts of undesirable by-products due to side reactions. In addition, a portion of the mercaptoalcohol usually distills together with the water. It has now been found that the disadvantages inherent in the prior art method can be avoided if the mercaptoalcohol is first reacted with the organotin compound and then esterified. Reactions of organotin halides and oxides with both mercaptans and alcohols are reported in the chemical literature. One would therefore expect a mixture of products containing tin-oxygen and tin-sulfur bonds. Surprisingly, under the conditions disclosed hereinafter only the mercaptide (—SH) portion of the mercaptoalcohol reacts with the organotin compound. The hydroxyl portion of the molecule remains available for subsequent esterification with a carboxylic acid.

SUMMARY OF THE INVENTION

This invention provides a method for preparing an organotin compound of the general formula

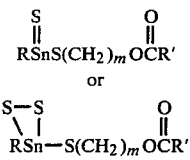

wherein R and R' are individually selected from the group consisting of alkyl containing from 1 to 20 carbon atoms, cycloalkyl, aralkyl, aryl and alkaryl and m is 2 or 3, said method consisting essentially of the following sequence of steps:

(1) reacting a monoorganotin trihalide of the formula $RSnX_3$ wherein X is a halogen selected from the group consisting of chlorine, bromine and iodine with an aqueous solution containing a stoichiometric amount, based on said monoorganotin trihalide, of a base selected from the group consisting of alkali metal hydroxides, alkaline earth metal hydroxides and ammonium hydroxide, wherein the ratio of the number of equivalent weights of base to the number of moles of monoorganotin trihalides is 1:1;

(2) adding an equimolar amount, based on said monoorganotin trihalide, of 2-mercaptoethanol or 3-mercaptopropanol to the resultant mixture;

(3) adding to the reaction product of step 2 an equimolar amount of an alkali metal sulfide or disulfide;

(4) separating the aqueous phase from the reaction mixture;

(5) reacting the product obtained thereby with an equimolar amount, based on said monoorganotin trihalide, of a carboxylic acid, R'COOH, or an ester R'COOR" wherein R" is alkyl and contains from 1 to 20 carbon atoms while removing any by-product water from the reaction mixture; and (6) isolating said organotin compound.

DETAILED DESCRIPTION OF THE INVENTION

The first step of the present method for preparing the present monoorganotin derivatives of mercaptoalcohol esters comprises reacting the corresponding monoorganotin trihalide of the formula $RSnX_3$ with an aqueous solution containing a stoichiometric amount of a base. All of the base can be added initially to react with the organotin halide. Alternatively, a major portion of base, usually about 90% of the total, is added initially and the remainder is added following addition of the alkali metal sulfide.

As disclosed in the preceding specification, the term X in the foregoing formulae represents chlorine, bromine or iodine and R represents an alkyl group containing from 1 to 20 carbon atoms, a cycloalkyl, aryl, alkaryl or an aralkyl group. When R is alkyl it can be methyl, ethyl, n-propyl, iso-propyl or any higher homolog containing up to 20 carbon atoms. Suitable cycloalkyl radicals include, for example, cyclopropyl, cyclobutyl, cyclohexyl and cyclooctyl. When R is aryl it is preferably phenyl but R may also represent naphthyl, anthrecenyl or biphenyl. Suitable aralkyl radicals include, for example, benzyl and β-phenylethyl. When R is alkaryl it can be, for example one of the isomeric tolyl, xylyl or other alkyl-substituted phenyl radicals.

The base employed is ammonium hydroxide, an alkali metal hydroxide, such as sodium hydroxide, or an alkaline earth metal hydroxide, for example calcium hydroxide.

The term "stoichiometric amount" is defined as one mole of a monofunctional base, such as sodium hydroxide, or 0.5 mole of a difunctional base, such as calcium hydroxide, for each mole of monoorganotin trihalide.

The reaction between the halogen atoms of the organotin halide and the base is rapid at ambient temperature and often highly exothermic. The addition of the organotin halide should therefore be gradual and the reaction mixture is simultaneously stirred and cooled to prevent localized overheating. It may be desirable to continue stirring the reaction mixture after all of the organotin halide has been added in order to improve heat transfer and increase the rate of cooling. The resultant solution of an organotin hydroxyhalide is then reacted with the desired mercaptoalcohol. The rate of this reaction is considerably slower than the rate at which the initial organotin halide reacts with a base. It may therefore be desirable to maintain the mixture at a temperature from 40° to 100° C. to complete the reaction in a reasonable length of time, usually from 5 to 60 minutes. The number of moles of mercaptoalcohol added is equal to the number of equivalent weights of base employed in the initial step of this method.

The most readily available mercaptoalcohols are 2-mercaptoethanol and 3-mercaptopropanol. These compounds are therefore preferred for use in the present method. Other known mercaptoalcohols, for example 4-mercapto-1-butanol, would be equally suitable.

When the reaction of the organotin compound with the mercaptoalcohol is completed, the resultant mixture is combined with one mole of an alkali metal sulfide for every mole of tin present in the reaction mixture when the final product contains 2 sulfur atoms per molecule. When the product contains 3 sulfur atoms an equimolar amount of an alkali metal disulfide is employed. The disulfide can be formed by reacting equimolar amounts of alkali metal sulfide and elemental sulfur. Preferably the sulfide or disulfide is added to the organotin component gradually, since the reaction may be exothermic. The sulfide or disulfide can be added as a solid or in an aqueous solution. Any base not added during the initial hydrolysis of the halide is added at this time.

Following the completion of the sulfide addition the mercaptoalcohol residue is esterified by addition of an equimolar amount of the desired carboxylic acid, R'COOH, or an ester thereof, R'COOR", derived from an alcohol containing from 1 to 20 carbon atoms. Suitable acids contain from 2 to 20 carbon atoms and the hydrocarbon residue is alkyl, cycloalkyl, aryl, aralkyl or alkaryl as previously disclosed for the hydrocarbon portion of the organotin halide reactant. R' may contain one or more substituents such as halogen, hydroxyl, alkoxy and nitro ($NO_2$) groups. In contrast to conventional esterification reactions, a stoichiometric excess of carboxylic acid is not required, nor is it necessary to add a catalyst. Octanoic acid, also known as caprylic acid, is preferred in that products prepared using this acid do not exhibit the disagreeable odor which characterizes this class of organotin compounds. If an ester of the acid is employed, the alcohol residue preferably contains from 1 to 4 carbons to facilitate removal of the alcohol by distillation during the transesterification reaction. In those instances when the final organotin compound will be used as a stabilizer for halogenated polymers such as polyvinyl chloride it may be desirable to employ a higher molecular weight alcohol containing from 12 to 20 carbon atoms as the alcohol component of the aforementioned ester R'COOR". In this instance the alcohol R"OH would not be removed during the transesterification, but rather is isolated together with the final organotin product. The alcohol serves as a lubricant or processing acid in the stabilized halogenated polymer composition.

Once the acid or ester has been added the aqueous phase of the reaction mixture is removed and discarded. Following removal of the aqueous phase, the reaction mixture is heated to 100°–180° C. to effect the esterification or transesterification reaction. If the by-product is water or a volatile alcohol boiling below about 120° C., the by-product is continuously removed during the reaction using a suitable distillation apparatus. To minimize overheating and the accompanying product decomposition the final portion of water is preferably removed under a reduced pressure that is usually equivalent to 10–100 mm. of mercury. Once all of the water or alcohol has been removed the final liquid organotin compound remains in the reaction vessel. It may be necessary to filter the product to remove small amounts of solid materials.

The products obtained using the present method are useful for the same applications as other mono- and di-organotin compounds containing tin-sulfur bonds. The present compounds are particularly effective heat stabilizers for vinyl chloride polymers and other high molecular weight halogen-containing polymers. The compounds are conventionally employed for this purpose at concentrations of from 0.1 to 10% by weight. Organotin derivatives of mercaptoalcohol esters may also find use as antioxidants for a variety of materials. The following examples demonstrate preferred embodiments of the present method and, as such, should not be interpreted as limiting the scope of the accompanying claims.

EXAMPLE 1—Preparation of
Monobutyltin-2-mercaptoethylcaprylate Sulfide

A reaction vessel was charged with 141.1 g (0.5 mole) of monobutyltin trichloride and 150 cc water. To the resultant solution is gradually added 29.0 g (0.5 mole) of ammonium hydroxide at a rate sufficient to maintain the temperature of the reaction mixture at or below 60° C. without external cooling of the reactor. Stirring of the reaction mixture was continued for five minutes following completion of the ammonium hydroxide addition, at which time 39.85 g (0.5 mole) of 2-mercaptoethanol was added to the contents of the reactor and the contents were stirred and heated to a temperature of 60° C. for ½ hour. The reaction mixture was then allowed to cool to 40° C. and 65.0 g (0.5 mole) of solid sodium sulfide was added at a rate such that the temperature of the reaction mixture did not exceed 60° C. The reaction mixture was stirred for 20 minutes following completion of the addition and the temperature was maintained at 60° C. using external heating. A 79.12 g (0.5 mole) portion of methyl caprylate was then added to the reaction and the contents were stirred for ten minutes, after which the aqueous phase of the reaction mixture was removed and discarded. The organic phase was heated at 140° C. under a nitrogen atmosphere using a distillation apparatus until the evolution of methanol ceased. The reaction mixture was then cooled and filtered to yield relatively pure monobutyltin-2-mercaptoethylcaprylate sulfide. This compound did not exhibit the offensive odor characteristic of monoorganotin or diorganotin derivatives of mercaptoethanol esters. An unpleasant odor is present for analagous compounds wherein the aforementioned n-octanoic acid ester is replaced by the oleic ester of 2-mercaptoethanol. This difference in odor is also true for the corresponding methyltin derivatives. These compounds are prepared by reacting methyltin trichloride in place of the corresponding butyltin chloride.

What is claimed is:

1. A method for preparing an organotin compound of the general formula

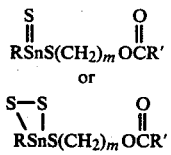

or

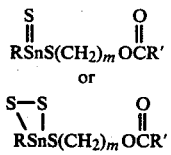

wherein R and R' are individually selected from the group consisting of alkyl containing from 1 to 20 carbon atoms, cycloalkyl, aralkyl, aryl and alkaryl and m is 2 or 3, said method consisting essentially of the following sequence of steps:

(1) reacting a monoorganotin trihalide of the formula $RSnX_3$ wherein X is a halogen selected from the group consisting of chlorine, bromine and iodine, with an aqueous solution containing a stoichiometric amount of a base selected from the group consisting of ammonium hydroxide, alkali metal hydroxides and alkaline earth metal hydroxides, wherein the ratio of the number of equivalent weights of base to the number of moles of monoorganotin trihalide is 1:1;

(2) adding an equimolar amount, based on said monoorganotin trihalide, of 2 mercaptoethanol or 3-mercaptopropanol to the resultant mixture;

(3) adding to the reaction product of step 2 an alkali metal sulfide or an alkali metal disulfide, the numbger of moles of sulfide or disulfide being equal to the number of moles of tin present in said reaction product;

(4) separating an aqueous phase from the reaction mixture;

(5) reacting the product obtained thereby with an equimolar amount, based on said monoorganotin trihalide, of a carboxylic acid, R'COOH, or an ester R'COOR" wherein R" is alkyl and contains from 1 to 20 carbon atoms, while removing any by-product water from the reaction mixture; and (6) isolating said organotin compound in the form of the liquid residue remaining following removal of said by-product water.

2. A method as set forth in claim 1 wherein R and R' are individually selected from the group consisting of alkyl radicals containing from 1 to 20 carbon atoms.

3. A method as set forth in claim 2 wherein R is butyl.

4. A method as set forth in claim 1 wherein said carboxylic acid is caprylic acid or pelargonic acid.

5. A method as set forth in claim 1 wherein m is 2.

6. A method as set forth in claim 1 wherein X is chlorine.

7. A method as set forth in claim 1 wherein the base reacted with the organotin halide is ammonium hydroxide.

8. A method as set forth in claim 1 wherein the alkali metal sulfide is sodium sulfide.

9. A method as set forth in claim 1 wherein R" contains from 1 to 4 carbon atoms.

10. A method as set forth in claim 1 wherein the alkali metal disulfide is formed by reacting equimolar amounts of said alkali metal sulfide and elemental sulfur.

11. A method as set forth in claim 1 wherein the product of step 3 is reacted with a carboxylic acid ester R'COOR" and the alcohol R"OH formed as a by-product of the reaction is removed by distillation prior to isolating said organotin compound.

* * * * *